US007777619B2

(12) United States Patent
Yopp et al.

(10) Patent No.: US 7,777,619 B2
(45) Date of Patent: Aug. 17, 2010

(54) SYSTEM AND METHOD FOR IMPLEMENTING ACTIVE SAFETY COUNTER MEASURES FOR AN IMPAIRED DRIVER

(75) Inventors: W. Trent Yopp, Canton, MI (US); Jeffrey Dan Rupp, Ann Arbor, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 506 days.

(21) Appl. No.: 11/786,110

(22) Filed: Apr. 11, 2007

(65) Prior Publication Data

US 2008/0252466 A1 Oct. 16, 2008

(51) Int. Cl.
*B60Q 1/00* (2006.01)

(52) U.S. Cl. ........................ 340/439; 340/576; 180/272

(58) Field of Classification Search ................ 340/439, 340/576, 309.15; 180/272; 361/170
See application file for complete search history.

(56) References Cited

U.S. PATENT DOCUMENTS 3,222,640 A 12/1965 Wurst
3,611,344 A 10/1971 Couper
3,824,538 A 7/1974 Slemp
4,209,075 A 6/1980 Messina
5,195,606 A 3/1993 Martyniuk
5,402,108 A * 3/1995 Tabin et al. ................ 340/575
5,465,079 A 11/1995 Bouchard et al.
5,570,087 A 10/1996 Lemelson
5,684,455 A * 11/1997 Williams et al. ............ 340/439
5,684,462 A * 11/1997 Gold .......................... 340/576
5,714,925 A * 2/1998 Lee et al. ................ 340/309.7
5,942,979 A 8/1999 Luppino
6,060,989 A 5/2000 Gehlot
6,154,123 A * 11/2000 Kleinberg .................. 340/436
6,426,702 B1 * 7/2002 Young et al. ................ 340/576
6,734,799 B2 5/2004 Munch
7,072,753 B2 7/2006 Eberle et al.
2005/0030184 A1 2/2005 Victor

* cited by examiner

*Primary Examiner*—Toan N Pham
(74) *Attorney, Agent, or Firm*—Franklin MacKenzie; Ford Global Technologies, LLC

(57) ABSTRACT

Various methods and systems are disclosed for implementing active safety countermeasures in vehicles when it is determined that the driver is impaired.

18 Claims, 3 Drawing Sheets

10 20 31 29 30 34 28 14 16 44 12 24 38 ECU 18 20 22 32 36 15 46 26 42 40

SYSTEM AND METHOD FOR IMPLEMENTING ACTIVE SAFETY COUNTER MEASURES FOR AN IMPAIRED DRIVER

BACKGROUND OF THE INVENTION

There are several active safety external sensing technologies that currently exist to improve safety and comfort of occupants and drivers of vehicles. For example, vehicles equipped with an adaptive cruise control with stop and go feature use long range sensors (i.e. radar and or lasers) to detect, track and provide path information to determine potential vehicle threat assessments. Based upon this information, vehicle speed and braking forces can be adjusted to reduce the risk of a collision. In addition, cameras are used to detect and classify objects of interest (vehicles, lane markers, road edges, etc.,) so that features can be activated (i.e., adaptive cruise control, blind spot detection, lane departure warning, etc.,) to improve driver comfort and awareness. There are also vehicle systems that control the power train, as well as the steering and braking functions. At the same time there are internal sensing technologies that monitor the driver to determine whether he/she is impaired. These types of systems provide a warning to alert the driver when it appears that he/she is impaired or non responsive to the alert warnings. However, in prior art systems, if the driver does not respond to the warning, there is usually nothing more that can be done. The same condition can exist when the driver has a sudden health concern. When these concerns arise, additional counter measures need to be taken to improve the safety of the driver and the vehicle's occupants and others that may be on or near the road by taking advantage of their vehicle system capabilities.

The present invention is directed to methods and systems for implementing active safety countermeasures that can determine whether the driver is alert and take active countermeasures as necessary in order to safeguard the driver, the vehicle occupants, and other that may be on or near the vehicle as it travels on the vehicle pathway.

BRIEF SUMMARY OF THE INVENTION

The present invention is directed to an active safety system for recognizing that the vehicle's driver is impaired and not responding to alert warnings and initials countermeasures to safeguard the vehicle occupants and others that may be on or nears the road. This is accomplished by first determining what other vehicle system capabilities are present on the vehicle (i.e., adaptive cruise control with stop and go; blind spot detection; traction control; steer by wire; external sensing-lane detection; path prediction; obstacle detection, etc.), and adapting the active safety feature accordingly. The system monitors the driver to determine whether the driver is not responding to the alert warning. If it is determined that the diver is not responsive to the alert warning, the method includes initialing counter measures such as adjusting safety restraints, in the case of pretension restraints, reducing vehicle speed via a message to the engine controller and/or the vehicle brakes, to a full stop. The system and method further contemplates activating the vehicle emergency warning lights and horn. These additional measures are initiated and tracked to bring the vehicle to a safe stop and warn others outside and inside the vehicle that the driver is no longer in control of the vehicle.

The method further contemplates, in vehicles equipped with external sensing and steering function capabilities (i.e., adaptive cruise control with stop and go; blind spot detection; traction control; steer by wire; external sensing-lane detection; path prediction; obstacle detection, etc.,) to process such external sensing data, determine if a safe path exists to travel to the side of the road and then assume control of the vehicle to travel the safe path to the side of the road and stop the vehicle out of the way of traffic.

DETAILED DESCRIPTION OF THE INVENTION

Figure 1:
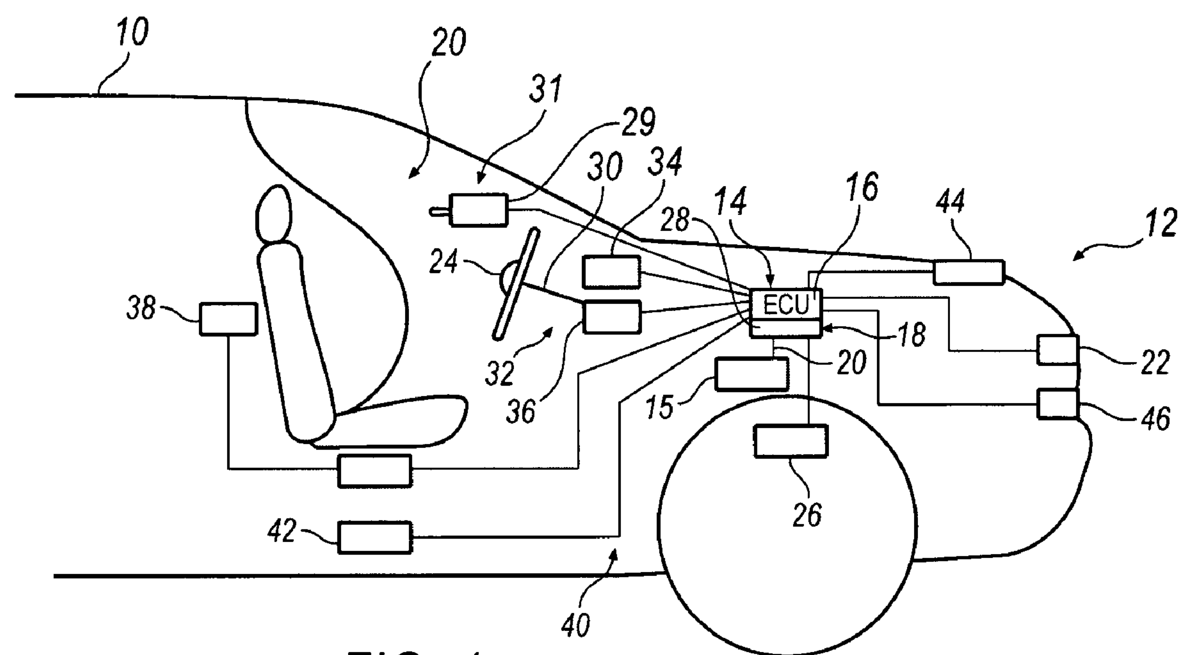
FIG. 1 is a schematic representation of a vehicle equipped with a system for initiating active safety countermeasure in the event the driver is impaired.

Turning now to the drawings wherein like numbers refer to like structures, and particularly to FIG. 1, vehicle 10 is equipped with active safety countermeasure system 12. The vehicle has an engine 15 with an engine control unit (ECU) 14 with a memory 16 which may be ROM, PROM, EPROM, EEPROM, Flash, or any other memory, wherein various tables 18 may reside. ECU 14 may also include various software programs that may control passive restraint systems 20, emergency flasher lights 22, horn 24, vehicle brakes 26, vehicle fueling 28 and vehicle steering system 30 whenever it is determined that the driver is impaired.

The vehicle may also include accessories 32 to assist in assessing the responsiveness of a driver. These may include auditory accessories 34, which may be speakers, piezo units or other devices capable of producing auditory warnings to the driver. Other accessories may include visual accessories 36, which may include lights or diodes or any other device capable of giving a visual warning to the driver. It is further contemplated that a feedback device 29 could be provided between the driver and the warning devices in order to permit the driver to demonstrate that he/she alert or has regained alertness and is able to operate the vehicle. This could be accomplished by having the driver activate manual switches 31 on the dashboard, or by voice command, eye motion or head position detection, or by any other device. Other accessories may include sensors 33 that can measure the biological functions of the driver such as heartbeat, breathing, perspiration, or even eye movement and head position in order to assist in the determination whether a driver is alert. The vehicle is also equipped with devices 40 for sensing driving state variables, such as motion detectors 42, cameras 44 and radar sensors 46. The cameras, motion detectors and radar sensors are used in vehicle equipped with external sensing to gather data and information about the surrounding area of the vehicle, and use the data to determine whether there are any other vehicles or objects in proximity to the vehicle that may pose a hazard or obstacle to the operation of the vehicle, and to implement steering control or to chart a path to the safe side of a road.

Figure 2:
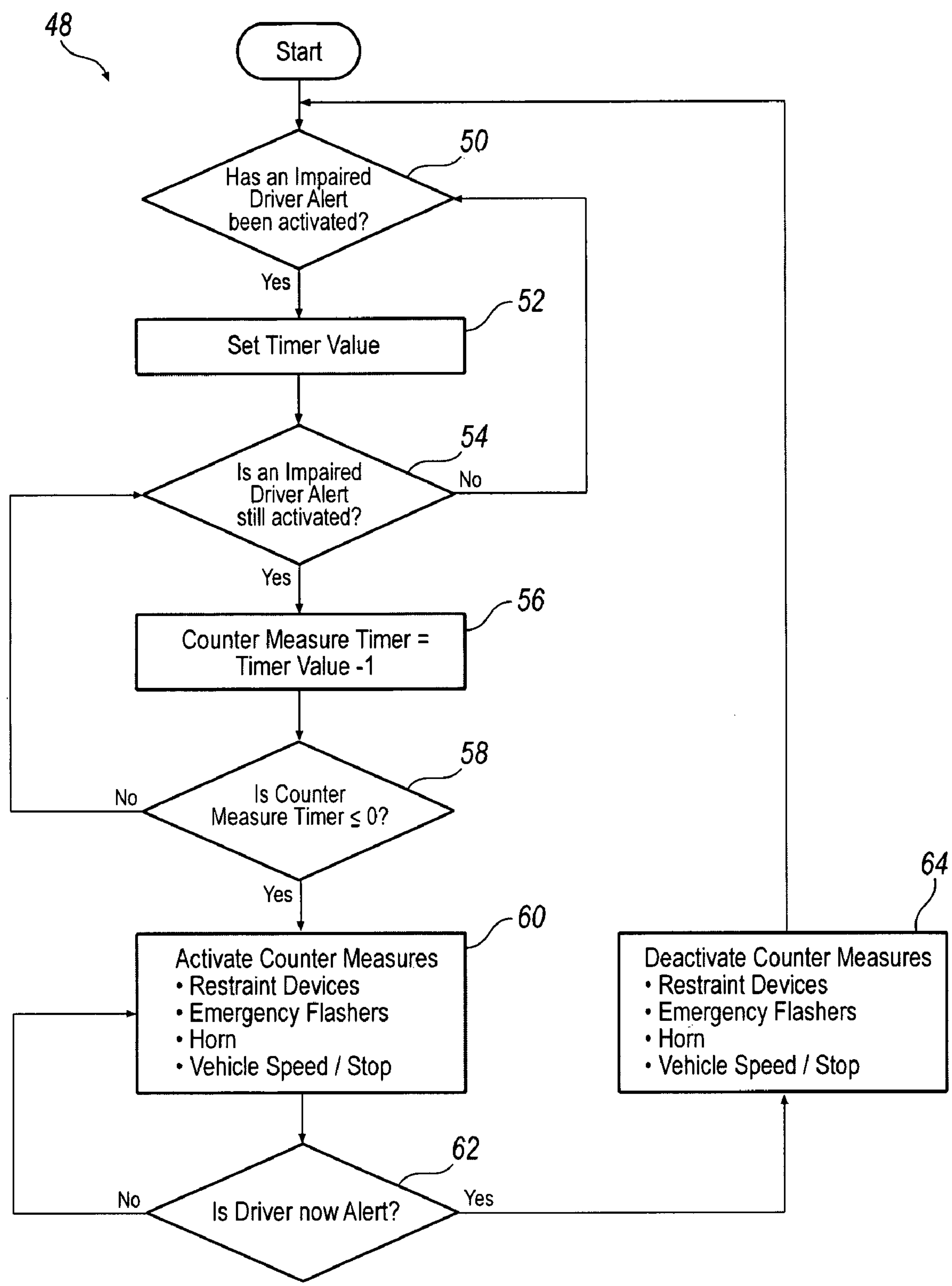
FIG. 2 is a representation of a software flow chart showing the steps in one aspect of the present invention.

FIG. 2 is a representation of a software flow chart for one aspect of the present invention. Specifically, in a vehicle that does not include devices 40 for sensing driving state variables, method 48 consists of a system to be used when a vehicle is equipped with an impaired driver detection system. Step 50 is determining whether an impaired driver alert has been activated. The impaired driver alert may be an auditory or a visual alert or any other alert to the driver that may require a driver to respond to the alert in a manner to disable the alert or otherwise respond to the alert is such a manner as to indicate that the driver is unimpaired and able to safely operate the vehicle. Step 52 is setting a timer value to the alert so that the driver has a fixed time within which to respond to the driver alert. Step 54 is determining whether the impaired driver alert is still activated. If not, the system has a loop back to step 52. If the impaired driver alert is determined to be activated beyond the set timer value, step 56 is a setting a counter measure timer value, within which time a countermeasure to the impaired driver situation will be activated. Step 58 is determining whether the counter measure timer value is less than or equal to 0. If it determined that the countermeasure timer is not less than or equal to 0, the method loops back to step 54. If it is determined that the counter measure timer is less than or equal to 0, step 60 is activating countermeasures to assist in the safe operation of the vehicle and the driver is protected while impaired. Examples of contemplated countermeasures include, but are not limited to, activating the passive restraints of the vehicle such as adjusting the tension on safety harnesses, activating the emergency flashers so that observers outside the vehicle are warned that the driver is impaired and no longer in control of the vehicle, sounding the horn so that persons outside the vehicle can hear the driver is impaired; adjusting the vehicle speed whereby fueling strategies within the ECM are implemented to slow the vehicle, and the vehicle brakes are activated to slow the vehicle. Step 62 is determining whether the driver is alert. If it is determined that the driver is not alert, the system loops back to step 60 and the active countermeasures are continued until the driver is alert. If and when it is determined that the driver is alert, step 64 is deactivating the active safety countermeasures to permit the driver to resume control of the vehicle and the system loops back to the beginning of the software system.

Figure 3:
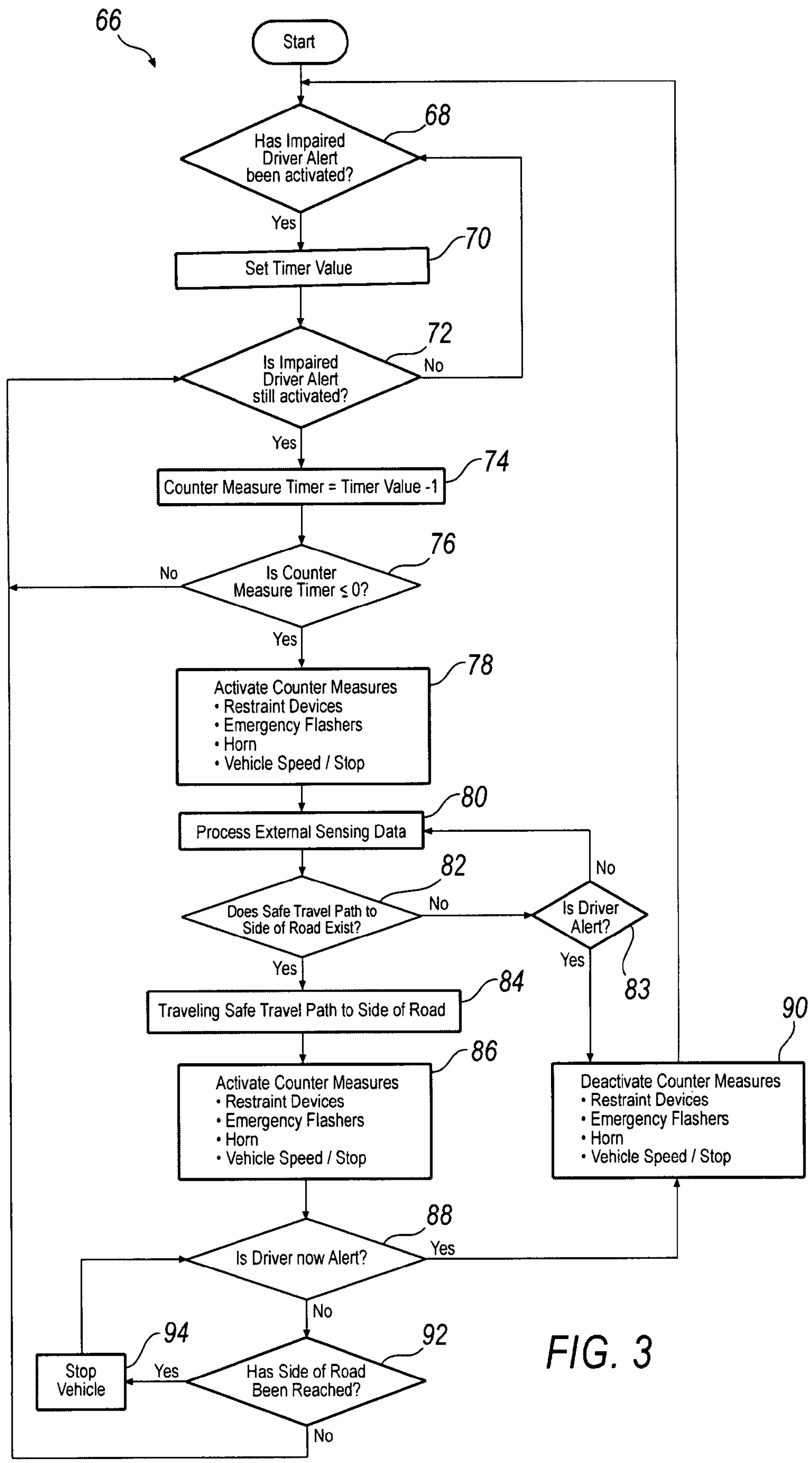
FIG. 3 is a representation of a software flow chart showing the steps in one aspect of the present invention.

FIG. 3 is another embodiment of the method for implementing active safety countermeasures of the present invention for vehicles with external sensing, steering and/or speed capabilities combined with impaired driver detection capabilities. Specifically, method 66 includes step 68, determining whether an impaired driver alert has been activated. In the event an impaired driver alert is activated, the software proceeds to Step 70, which is setting a timer value for the driver alert. Step 72 is determining whether the impaired driver alert is still activated. If it is determined that the impaired driver alert is not still activated, the software loops back to step 68. If it is determined that the impaired driver alert is still activated, step 74 is setting a countermeasure timer value, at which time a countermeasure to the impaired driver condition will be implemented. Step 76 is determining whether the countermeasure timer$\leqq$0. If it is determined that the counter measure timer is $\leqq$0, step 78 is activating counter measures such as restraint devices, emergency flashers, sounding the horn and limiting vehicle speed through fueling strategies and the like, and activating vehicle brakes to slow or stop the vehicle. This step is advantageous in the event it is determined later in the software that no safe travel path exists to the side of a road. However, in systems equipped with active steering and brakes, external data is gathered to assist in the determination of whether a safe path can be detected. This is accomplished in Step 80, which is processing external sensing data to determine a course of action for the operation of the vehicle while the driver is impaired, based upon sensed conditions. Once the external data is processed, step 82 is determining whether a safe travel path to the side of the road exists. If no safe path to the side of the road exists, step 83 determines is the driver alert? If yes, the software proceeds directly to step 90 deactivating countermeasures. If no, the software loops back to step 80. Once it is determined that a safe path to the side of the road exists, step 84 is traveling the safe travel path to the side of the road. This may be accomplished by using the sensed external data to control the steering, fueling and brakes of the vehicle to travel the safe travel path to the side of the road. Step 86 is activating vehicle safety countermeasures such as, but not limited to, adjusting the tension on passive restraints devices, activating the emergency flashers to alert outside observes that the driver is impaired and no longer in control of the vehicle; sounding the vehicle horn to alert persons with an auditory warning who have not seen the emergency flashers that the driver is impaired and no longer in control of the vehicle; activating the steering movements of the vehicle to steer the vehicle along the selected safe path to the side of the road and reducing the vehicle speed by controlling the fueling to the vehicle engine and/or activating the vehicle brakes in order to modulate the vehicle speed to a safe speed to protect the impaired driver. Step 88 is determining whether the driver is alert when the active counter measures are being undertaken. If it is determined that the driver has regained alertness, step 90 is deactivating active safety countermeasures to permit the driver the assume command of the vehicle and the software loops back to the beginning of the process. If it is determined that the driver is not alert, step 92 is determining whether the safe side of the road has been reached. If yes, step 94 is stopping the vehicle and the software loops back to step 88. If it is determined that the vehicle has not reached the side of the road, the software loops back to the step 74 to determine whether an impaired driver alert is still activated and then to the rest of the software as described above, to permit further processing of external sensed data to permit the vehicle to reach the safe side of the road.

Several systems and methods for activating safety countermeasures to control a vehicle if it is determined that the driver is impaired have been discussed. It is apparent that the words used herein are words of description and not words of limitation. Those skilled in the art will recognize that various modifications may be made to the systems and methods disclosed without departing from the scope and spirit of the invention as set forth in the appended claims.

What is claimed as new and desired to be protected by Letters Patent of the United States is:

1. A method for implementing active safety measures in a vehicle with an engine control unit having memory for controlling impaired driver detection, comprising:

determining whether a driver alert signal has been activated;

setting a time value for the alert signal;

determining whether the alert signal is still activated;

setting a counter measure time value;

determining whether the counter measure time value$\leqq$0;

determining whether a road side has been reached if said driver is not alert;

activating counter measures to ensure driver safety.

2. The method of claim 1, wherein said vehicle active counter measures include restraining drivers, emergency flashers, vehicle horn, vehicle fueling, vehicle brakes.

3. The method of claim 1, further including determining whether the driver is alert and deactivating the active safety counter measures.

4. The method of claim 1, further including determining whether said impaired driver alert is activated if said counter measure time is greater than 0.

5. The method of claim 1, further including determining whether an impaired driver alert has been activated when said alert is not currently active.

6. The method of claim 1, further including stopping the vehicle once the vehicle has reached the side of the road.

7. The method of claim 6, further including determining whether the driver is alert after stopping said vehicle.

8. The method of claim 7, further including deactivating counter measures when driver is alert.

9. A method for activating active safety counter measures in a vehicle equipped with an engine control unit having memory for controlling external sensing, steering speed capabilities and impaired drive detection, comprising:

a) determining whether an impaired driver alert has been activated;

b) setting a time value for the impaired driver alert;

c) determining whether the impaired driver alert is still active beyond said time value;

d) determining a counter measure time value;

e) determining whether the counter measure time value≦0;

f) activating counter measures if countermeasure time value is ≦0;

g) processing external sensing, steering and speed data;

h) determining whether a safe travel path to side of a road upon which said vehicle is traveling exists;

i) traveling said safe path to the side of the road;

j) activating safety counter measures;

k) determining whether driver is alert;

l) controlling said vehicle fueling, steering and braking while traveling said safe travel path to the side of the road;

m) stopping said vehicle;

n) determining whether driver is alert;

o) deactivating active safety counter measures if it is determined the driver is alert.

10. The method of claim 9, further including determining whether the driver is alert and processing external sensing data if it is determined there is no safe path to side of the road.

11. The method of claim 9, further including determining whether the impaired driver alert is still activated if said counter measure time value is greater than 0.

12. The method of claim 9, wherein said active safety counter measures include restraint devices, emergency flashers, horn, steering movements, vehicle speed, vehicle fueling.

13. The method of claim 9, wherein said external sensing includes long range sensors to detect, track and provide path information to determine patented threat assessments to central vehicle speed and braking forces; cameras to detect and classify objects of interest; and systems to control the powertrain, steering and braking functions.

14. The method of claim 9, further including internal sensors to monitor driver condition.

15. A system for implementing active safety countermeasures in a vehicle when an impaired driver is detected, comprising: an electronic control unit (ECU) with memory wherein various tables and software may be resident; accessories to assist in assessing whether a driver is responsive; a passive restraint system controllable by said ECU when an impaired driver is detected; at least one external warning device to alert persons outside the vehicle that the driver is impaired; vehicle brakes controllable by a software in said ECU when an impaired driver is detected; and a vehicle fuel strategy controllable by software in said ECU when an impaired driver is detected.

16. The system of claim 15, further including a feedback device to permit the driver to demonstrate that he/she is not impaired.

17. A system for implementing active safety countermeasures when an impaired driver is detected in a vehicle equipped with external sensing, steering and speed capabilities, said system comprising: an Electronic Control Unit (ECU) with memory wherein various tables and software may be resident; said ECU controlling said system; accessories to assist in assessing whether a driver is responsive; a passive restraint system controllable by software in said ECU when an impaired driver is detected; at least one external warning device to alert persons outside said vehicle that the driver is impaired; vehicle brakes and vehicle fueling strategy controllable by said software when an impaired driver is detected.

18. The system of claim 17, further including a feedback device to permit said driver to demonstrate that he/she is not impaired.

* * * * *